United States Patent [19]

Fay

[11] Patent Number: 4,920,975

[45] Date of Patent: May 1, 1990

[54] BIOLOGICAL FLUID COLLECTION APPARATUS WITH THE CAP ON THE COVER

[75] Inventor: John E. Fay, Leominster, Mass.

[73] Assignee: Biomedical Polymers, Inc., Leominster, Mass.

[21] Appl. No.: 312,465

[22] Filed: Feb. 21, 1989

[51] Int. Cl.⁵ .............................................. A61B 5/00
[52] U.S. Cl. ................................................... 128/760
[58] Field of Search ................ 128/760, 763; 604/317; 435/296

[56] References Cited

U.S. PATENT DOCUMENTS

| | | | |
|---|---|---|---|
| 3,518,164 | 6/1970 | Andelin et al. | 128/760 |
| 4,064,760 | 12/1977 | Benjamin | 128/760 |
| 4,589,548 | 5/1986 | Fay | 128/760 |
| 4,741,346 | 5/1988 | Wong et al. | 128/760 |
| 4,761,379 | 8/1988 | Williams et al. | 128/760 |

Primary Examiner—Max Hindenburg
Attorney, Agent, or Firm—Joseph S. Iandiorio

[57] ABSTRACT

An apparatus for collecting biological fluid includes a container having an open end and a closed end; a funnel including a mouth at one end and a discharge portion at the other end, the discharge portion being removably attachable to the container to establish fluid communication between the funnel and the container; a cap for closing the container opening; a cover for the mouth of the funnel, which cover has a chamber for releasably holding the cap with the inside of the cap facing outward for engaging with the container opening; and a base having a top which includes a container recess for receiving the closed end of the container to support at least a portion of the container above the base.

14 Claims, 3 Drawing Sheets

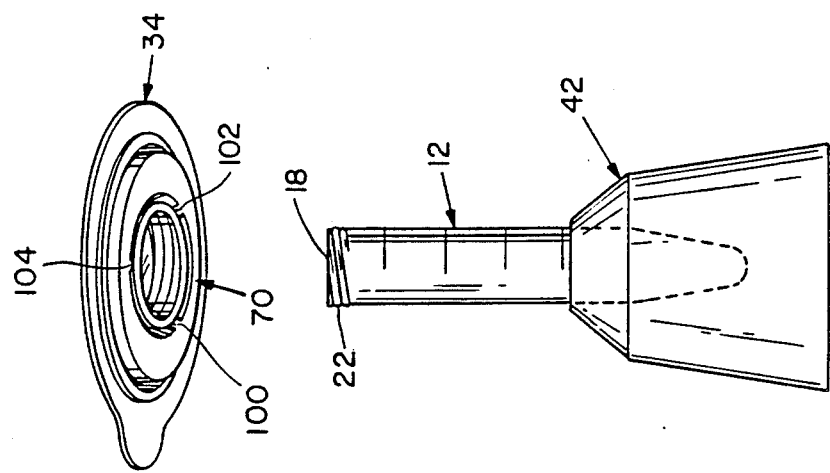
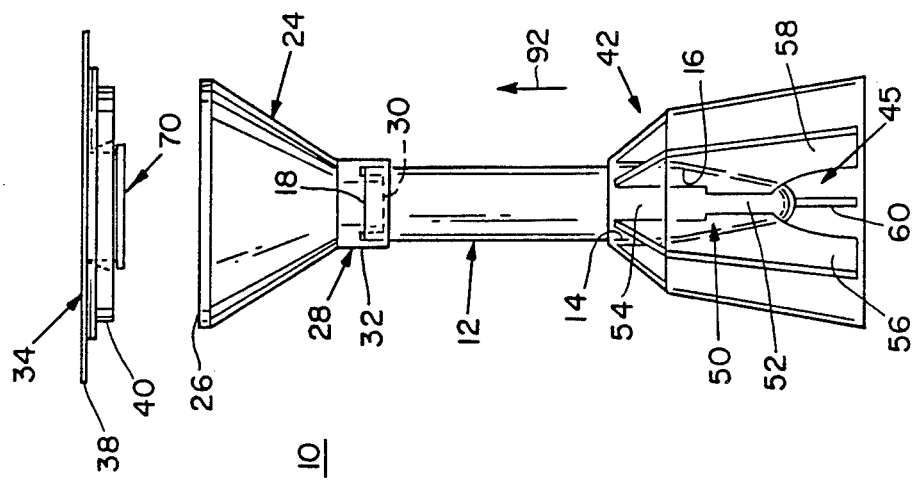
Fig. 3
Fig. 2

BIOLOGICAL FLUID COLLECTION APPARATUS WITH THE CAP ON THE COVER

FIELD OF INVENTION

This invention relates to an apparatus for safely collecting biological fluids such as sputum specimens for testing and diagnosis, and more particularly to such an apparatus which provides a self-contained cap for sealing the collection container.

BACKGROUND OF INVENTION

Biological fluids are required for diagnosis of many ailments. For example, the diagnosis of tuberculosis and other respiratory ailments necessitates the taking of sputum samples for testing and analysis. Such specimens are typically collected by a doctor, nurse or laboratory technician using one of a number of known sputum collection systems.

An important requirement of any collection system is that it minimize the risk of contamination of hospital or lab personnel who handle the device. In an effort to reduce this danger, one device of the prior art employs a graduated cylinder having a funnel attached at one end. A protective outer body encloses the cylinder entirely and attaches to the funnel. The cylinder is mounted within an annular ring on a removable bottom lid of the enclosure. A threaded cap is mounted sideways on the inside wall of the enclosure. After the specimen has been collected, the funnel and cylinder are removed from the enclosure and the bottom lid is opened. The open end of the cylinder is inserted into the bottom of the enclosure, and the cylinder is tilted to engage the cap and slide it out of the enclosure and loosely onto the cylinder. The cap is then tightened by hand on the cylinder and centrifuging and testing are performed. The enclosure and funnel are both discarded.

This collection system exhibits a number of disadvantages. For example, it is complex and awkward to use. Because of the sideway position of the cap in the enclosure, it is very difficult to thread the cylinder directly onto the cap while that cap is still in the enclosure. Therefore, the cap must often be slid out of the enclosure and hand-tightened. An extra time-consuming step is thus added, and the lab technician's hands are exposed to the risk of inadvertently contacting the open end of the sputum-containing cylinder. Moreover, sliding the cap out of the receptacle is a very delicate maneuver and it is quite easy for the cap to slip off the cylinder and drop to the floor, where it may be readily contaminated.

The large enclosure presents additional problems. Although the bottom of the enclosure flares slightly, the large longitudinal enclosure still presents a relatively high center of gravity. The device is therefore unstable and tends to tip over when it is transported on a hospital cart, tray or similar apparatus. Furthermore, when the enclosure and funnel are removed the annular ring in the bottom lid is insufficient to independently hold the cylinder upright. The enclosure and funnel are themselves discarded, and in any event it is unsanitary, awkward and wholly impractical to reassemble the enclosure to enable the capped cylinder to stand upright. Therefore, a separate rack is required for storing or transporting the specimen-containing cylinder. Additionally, the size of the enclosure adds to the complexity and costs of manufacturing the device.

More recently collectors have been disclosed which mount the cap horizontally in the base, but these designs too have serious shortcomings: the open container holding the fresh specimen must be pulled out of the base before it can have its open upper end presented to the cap located in the bottom of the base. This action can splash or spill the specimen a serious problem in the present atmosphere of fear engendered by AIDS. The container must be removed from the base after the specimen is collected to enable capping; then the container must be re-inserted in the base for transport to a laboratory for analysis. In addition, there is constantly a tendency to tilt the container to engage it with the cap in the base. This too promotes the danger of spilling the fresh specimen.

SUMMARY OF INVENTION

It is therefore an object of this invention to provide an improved biological fluid collection apparatus.

It is a further object of this invention to provide a biological fluid collection apparatus which permits the operator to quickly, easily and safely cap the specimen container without removing the container from its base.

It is a further object of this invention to provide a biological fluid collection apparatus which is simply and efficiently constructed and relatively inexpensive to manufacture.

It is a further object of this invention to provide a biological fluid collection apparatus which provides stable support for a capped specimen container during transportation and storage without the need for a separate laboratory rack.

It is a further object of this invention to provide a biological fluid collection apparatus in which the sputum can be collected in the container, the container can be capped, and the capped container can be transported in the base without the container ever being removed from the base.

The invention results from the realization that an improved, safer biological fluid collection apparatus can be achieved by providing a cap provisionally secured in the cover of the funnel of the collection container so that the cap is always available and ready for sealing the container as soon as the specimen has been collected and without removing the container from its base.

This invention features an apparatus for collecting biological fluid which includes a container having an open end and a closed end. There is a funnel which includes a mouth at one end and a discharge portion at the other end. The discharge portion is removably attachable to the container to establish fluid communication between the funnel and the container. A cap is provided for closing the container opening. There is a cover for the funnel. The cover includes a cap chamber for releasably holding the cap with the inside of the cap facing outward for engaging with the container opening. A base is provided having a top which includes a recess for receiving the closed end of the container to support at least a portion of the container above the base.

In a preferred embodiment the container is elongate and includes a tube having graduated indicia thereon. The tube may include thread means proximate the open end thereof, and the cap may include complementary thread means for engaging the thread means of the tube to close the tube with the cap.

An upper lid may be provided for selectively closing the mouth of the funnel. The cover may include ridge means disposed on the inside surface thereof and receivable within the mouth of the funnel for sealably engaging the inner surface of the funnel.

The discharge portion of the funnel may include an inner lip receivable within the opening of the container for sealably engaging the inner wall of the container, and an outer peripheral lip arranged coaxially with the inner lip for receiving the open end of the container and sealably engaging the outside surface of the container.

The container recess may include a lower generally conical section and an upper generally cylindrical section for receiving mating conical and cylindrical sections of the container. The means for holding typically includes means for gripping the periphery of the cap. Such means for gripping preferably includes a plurality of radial projections spaced about the cap chamber and extending inwardly from the wall of the cap chamber to engage the periphery of the cap and provide a friction fit between the cap and the projections. Three such radial projections may be employed. Each projection may include a first surface for engaging the peripheral surface of the cap and a second surface for engaging the top surface of the cap. Typically the means for holding locates the cap centrally within the cover.

DISCLOSURE OF PREFERRED EMBODIMENT

Other objects, features and advantages will occur from the following description of a preferred embodiment and the accompanying drawings, in which:

FIG. 2 is an elevational view of the collection apparatus of FIG. 1 with the cover raised ready for collection of a specimen of sputum or other biological fluid;

FIG. 3 is an axonometric view illustrating the manner in which the tubular container still in the base is threadably attached to the cap located within the cover of the device.

Figure 1:
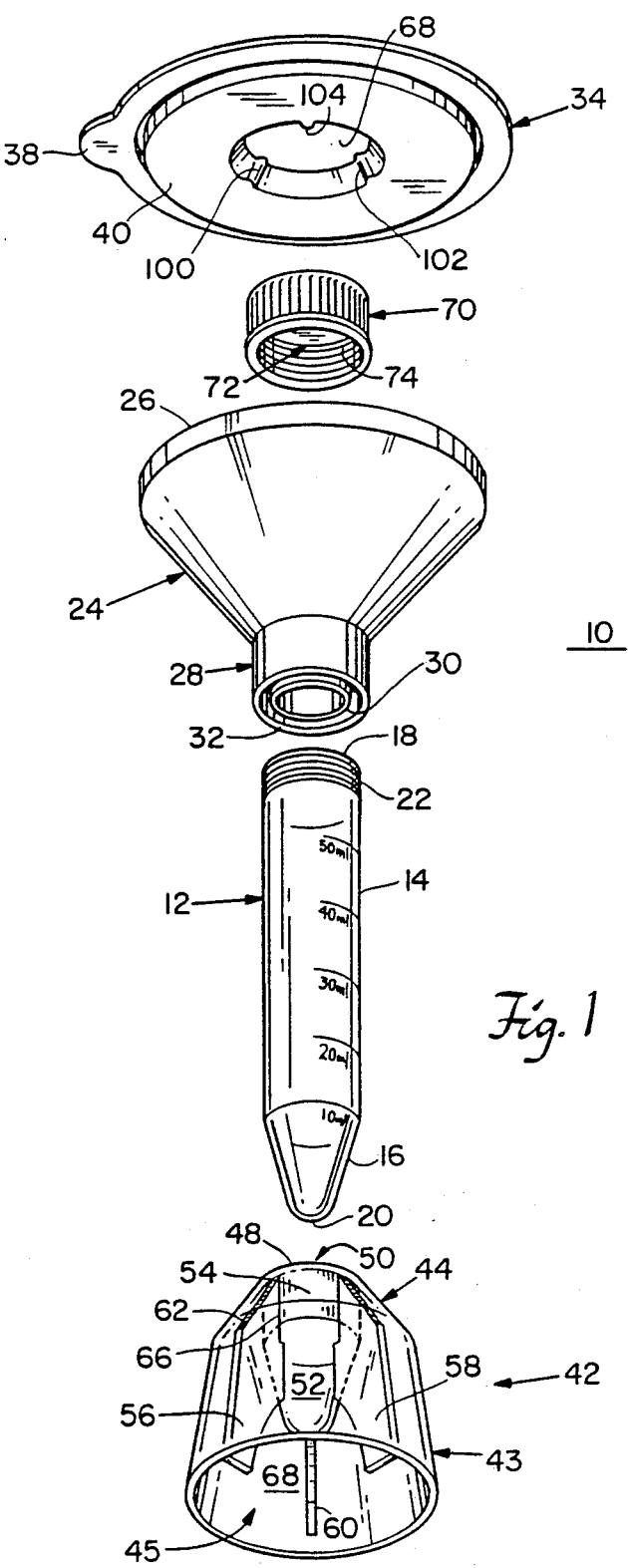
FIG. 1 is an exploded view of a biological fluid collection apparatus according to this invention.

A collection apparatus for biological fluid according to this invention may be accomplished using an elongate tubular container which serves to hold the collected specimen. The container is typically a graduated (e.g., 50 ml) test tube which may be conveniently employed for centrifuging and other lab tests. The tube is typically translucent to permit enhanced observation. It preferably includes a conical, closed lower end and an open cylindrical upper end having peripheral threads to permit attachment of a threaded cap. The cap may be transparent or opaque.

A funnel which includes a mouth at one end and a discharge portion at the other end is also provided. The discharge portion is removably attachable to the container to establish fluid communication between the funnel and the container. The discharge portion of the funnel typically includes an inner annular lip which is receivable within the opening of the tubular container and which sealably engages the inner wall of that container. The discharge portion also includes an outer peripheral lip which is arranged coaxially with the inner lip and which itself receives the open end of the container and sealably engages with the outside surface thereof. A cover is provided for the funnel. The cover selectively opens and closes the mouth of the funnel. It preferably includes ridge means on the inside surface thereof which is receivable within the mouth of the funnel and which sealably engages the inner surface of the funnel.

The ridge means provided on the inside surface of the upper lid provides a very effective seal for the mouth of the funnel. Likewise, the inner and outer annular lips of the discharge portion of the funnel provide a very effective seal with the upper open end of the specimen tube. The discharge portion provides sealing engagement with both the inner and outer surfaces of the specimen tube. Sealing is enhanced and the risk of contamination is thereby lessened.

The tubular container and attached funnel are supported by a base having a top which includes a recess for receiving the closed end of the container. At least a portion of the container extends above the base. The recess preferably includes a lower, generally conical section for receiving the mating conical closed end of the container, and an upper, generally cylindrical section for receiving the mating cylindrical section of the container. The bottom of the base may be open or closed. Means are mounted within a chamber in the cover for releasably holding the cap, with the inside of the cap facing the funnel mouth. It is preferred that such means for holding include means for gripping the periphery of the cap. The means for gripping may be a plurality of radial projections spaced about the chamber and extending inwardly from the wall thereof to provide a friction fit between the cap and the cover. Typically three such projections are provided, although more or less than three projections are certainly within the scope of this invention. The means for holding typically locates the cap centrally within the cover.

Such a construction is clearly advantageous over devices of the prior art. It enables the cap in the cover to be directly threaded onto the container filled with the specimen without ever removing the container from the base. This eliminates independent handling of the container which increases the potential for spilling or splashing the specimen sample in the yet uncapped container. It also avoids pulling the uncapped container from the base, which also can cause jerking and spilling. Further, the tube need not be tilted and there is no need to delicately slide the cap out of a slot or to manually touch or tighten the cap in any manner. Furthermore, the risk of inadvertently dropping the cap is reduced.

The base provides for enhanced stability for the collection apparatus. The base exhibits a much lower center of gravity than is provided by the full-length enclosures of previous devices. The apparatus is less likely to tip over as it is being transported in hospital or lab trays or carts. The construction of the base also permits it to be conveniently used as a storage or transporting holder for a capped specimen container. At all times, during collection of the biological fluid such as sputum, during capping of the container, and afterward, the specimen container remains within the base without the need for removal and reinsertion. After collection of the sputum the funnel is no longer needed. The capped specimen-containing tube in the base may then be transported on a hospital tray, or stored, for example in a refrigerator, without the necessity of a separate test tube rack.

For simplicity of manufacture, the container and cap, as well as the funnel, base and the cover, may be composed of a transparent material such as plastic. The molding and manufacture of the apparatus is thus greatly simplified. Although the device of this invention is suited for collection of any biological fluid, it is explained in the preferred embodiment as a sputum collection apparatus.

There is shown in FIG. 1 a sputum collection device 10 which includes a translucent 50 ml tubular container 12 having a cylindrical portion 14 and a conical portion 16. Cylindrical portion 14 includes an open end 18 and conical portion 16 terminates in a closed lower end 20. Threads 22 are disposed circumferentially about cylindrical portion 14 proximate open end 18.

Funnel 24 includes a large mouth 26 at one end and a discharge portion 28 at the other end. Discharge portion 28 includes an inner annular lip 30 which is receivable within open end 18 of container 12 and a peripheral lip 32 which is arranged coaxially with lip 30 and which receives open end 18 of container 12. Cover 34 includes a tab 38 for grasping the lid and circular ridge means 40 spaced from the edge of the lid.

Hollow base 42 includes a lower section 43 which has a slight converging taper from bottom to top and an upper section 44 which exhibits a much greater converging taper from bottom to top. The top 48 of base 42 includes a recess 50 which extends into volume 45. Recess 50 includes a lower conical section 52 for receiving mating conical portion 16 of container 12. Recess 50 also includes an upper cylindrical section 54 for receiving mating cylindrical section 14 of container 12.

Three reinforcing elements 56, 58 and 60 are mounted within base 42. For example, as illustrated by element 56, each projection element includes an edge 62 which engages upper section 44 of base 42, an edge 64 that engages base 42, and an edge 66 which engages the upper cylindrical section 54 of recess 50. The projection element may be secured within the chamber by applying glue or epoxy between any of these respective lines of engagement. Alternatively, the projection elements may be made integral with the base. The projection elements 56, 58 and 60 extend radially partially inwardly from the walls of base 42.

Cover 34 includes a chamber 68 within which cap 70 may be accommodated so that the inside 72 of cap 70 faces mouth 26 of funnel 24. The inside periphery of cap 70 includes threads 74. Chamber 68 includes a number of radially extending projections 100, 102, 104, spaced about the chamber 68 and extending inwardly from the wall thereof to provide a friction fit between the cap 70 and cover 34.

As shown in FIG. 2, when funnel 24 is mounted on container 12, the inside annular lip 30 of discharge portion 28 is received within the open end 18 of container 12 and sealably engages the inside surface of the tubular container. Container 12 is itself received within peripheral lip 32 of discharge portion 28 which sealably engages the outer surface of the container, and specifically the threads 22 thereof. Such inner and outer sealing of the open end 18 of container 12 insures against accidental specimen leakage and/or contamination of the operator or outside of the container.

Container 12 is inserted into recess 50 of base 42 so that conical container section 16 mates with conical recess section 52 and cylindrical container section 14 mates with cylindrical recess section 54. The remainder of cylindrical section 14 of container 12 extends above base 42.

Cap 70 is disposed centrally within chamber 68 and is peripherally gripped therein so that the inside of the cap faces the mouth 26 of funnel 24 when cover 34 is closed. Specifically, cap 70 fits within the space defined by elements 100, 102, and 104.

To collect a specimen, tab 38 is grasped and cover 34 is removed. The patient then deposits the sputum sample into the funnel 24 so that it is conducted into container 12. Cover 34 is replaced so that ridge means 40 are received by funnel mouth 26 and sealably engage the inside surface of the funnel 24 proximate mouth 26.

When collection of the specimen has been completed, FIG. 3, cover 34 is kept but the funnel is removed from container 12 and discarded. Container 12 remains supported in base 42. As shown in FIG. 3, lower lid 76 is opened, thereby exposing the inside of cap 70. Operator 0 grasps cover 34 in one hand and base 42 supporting container 12 in the other, and simply engages the open end 18 of container 12 with the inside 72 of centrally located cap 70. Cover 34 with cap 70 is rotated to engage the threads 22 of container 12 with threads 74 of cap 70. The cap is thereby secured to the container. The capped container is then simply and safely pulled out of base 42.

Figure 4:
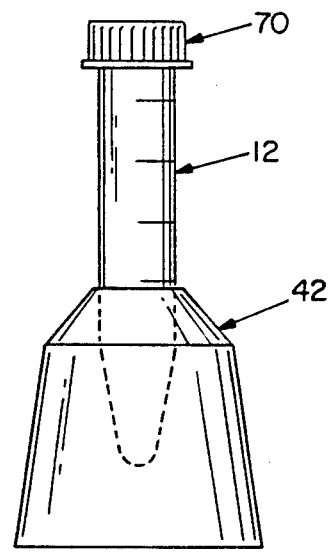
FIG. 4 is an elevational view of a capped container still supported within the base for transportation or storage.

Although the capped container 12 may then be accommodated by a test tube rack or similar device until it is needed for centrifuging or other testing, base 42 may also be used as such as holder. As shown in FIG. 4, capped container 12 is still in the recess within base 42. The capped container and base may be placed on a hospital cart for transport or in a refrigerator or other storage area. The relatively low center of gravity of base 42 enables the device to resist tipping. Need for a separate test tube rack is thus eliminated.

Although specific features of the invention are shown in some drawings and not others, this is for convenience only as each feature may be combined with any or all of the other features in accordance with the invention.

Other embodiments will occur to those skilled in the art and are with the following claims:

What is claimed is:

1. An apparatus for collecting biological fluid comprising:
   a container having an open end and a closed end;
   a funnel including a mouth at one end and a discharge portion at the other end, said discharge portion being removably attachable to said container to establish fluid communication between said funnel and said container;
   a cap for closing the container opening;
   a cover for the mouth of said funnel, said cover having a chamber for releasably holding said cap with the inside of the cap facing outward for engaging with the container opening; and
   a base having a top which includes a container recess for receiving the closed end of said container to support at least a portion of said container above said base.

2. The apparatus of claim 1 in which said container is elongate.

3. The apparatus of claim 1 in which said container is a tube.

4. The apparatus of claim 3 in which said tube includes graduated indicia thereon.

5. The apparatus of claim 3 in which said tube includes thread means proximate the open end thereof and said cap includes complementary thread means for engaging the thread means of said tube to close said tube.

6. The apparatus of claim 1 in which said cover includes means for interconnecting with said funnel.

7. The apparatus of claim 6 in which said cover includes ridge means disposed on the inside surface thereof and receivable within the mouth of said funnel for sealably engaging with the inner surface of said funnel.

8. The apparatus of claim 1 in which said discharge portion includes an inner annular lip receivable within the opening of said container and an outer peripheral lip arranged coaxially with said inner lip for receiving the open end of said container and sealably engaging the outside surface of said container.

9. The apparatus of claim 1 in which said container recess includes a lower generally conical section and an upper generally cylindrical section for receiving mating conical and cylindrical sections of said container.

10. The apparatus of claim 1 in which said chamber includes means for gripping the periphery of said cap.

11. The apparatus of claim 10 in which said means for gripping includes a plurality of radial projections spaced about said chamber and extending inwardly to provide a friction fit between said cap and said projections.

12. The apparatus of claim 11 in which said means for gripping includes three radial projections.

13. The apparatus of claim 1 in which said chamber locates said cap centrally within said cover.

14. An apparatus for collecting biological fluid comprising:
a tubular container having an open end and a closed end;
a funnel including a mouth at one end and a discharge portion at the other end, said discharge portion being removably attachable to said container to establish fluid communication between said funnel and said container;
a cap for closing the container opening;
a cover for the mouth of said funnel, said cover having a chamber for releasably holding said cap with the inside of the cap facing outward for engaging with the container opening; and
a base having a top which includes a container recess for receiving the closed end of said container to support at least a portion of said container above said base.

* * * * *